United States Patent
Giammarusti

(10) Patent No.: US 6,795,727 B2
(45) Date of Patent: Sep. 21, 2004

(54) DEVICES AND METHODS FOR PROMOTING TRANSCUTANEOUS MOVEMENT OF SUBSTANCES

(76) Inventor: Pedro Giammarusti, Al. Xian, 266-Tamboré 111, Santana de Parnaiba-SP-06490-540 (BR)

(*) Notice: Subject to any disclaimer, the term of this patent is extended or adjusted under 35 U.S.C. 154(b) by 11 days.

(21) Appl. No.: 09/978,883

(22) Filed: Oct. 17, 2001

(65) Prior Publication Data

US 2003/0073949 A1 Apr. 17, 2003

(51) Int. Cl.$^7$ .............................................. A61N 1/30
(52) U.S. Cl. ........................... 604/20; 604/19; 604/501
(58) Field of Search ............................. 604/19, 20, 21, 604/22, 27, 28, 30, 500, 501, 502, 93.01, 264, 523

(56) References Cited

U.S. PATENT DOCUMENTS

| | | | |
|---|---|---|---|
| 855,298 A | 5/1907 | Frost | |
| 3,551,554 A | 12/1970 | Herschler | 424/7 |
| 3,711,602 A | 1/1973 | Herschler | 424/45 |
| 3,711,606 A | 1/1973 | Herschler | 424/243 |
| 4,557,943 A | 12/1985 | Rosler et al. | 427/38 |
| 5,115,805 A | 5/1992 | Bommannan et al. | 128/24 |
| 6,009,346 A | * 12/1999 | Ostrow | 604/20 |
| 6,219,577 B1 | * 4/2001 | Brown et al. | 604/20 |
| 6,410,046 B1 | * 6/2002 | Lerner | |

FOREIGN PATENT DOCUMENTS

| | | |
|---|---|---|
| EP | 0 043 738 A2 | 1/1982 |
| EP | 0 043 738 B1 | 10/1985 |

OTHER PUBLICATIONS

Tachibana, K. "Transdermal Delivery of Insulin to Alloxan–Diabetic Rabbits by Ultrasound Exposure", Pharmaceutical Research, 1992; 9(7):952–954.

Byl, N. "The Use of Ultrasound as an Enhancer for Transcutaneous Drug Delivery: Phonophoresis", Physical Therapy, Jun. 1995; 75(6):539–553.

Griffin, J. et al. "Patients Treated with Ultrasound Driven Hydrocortisone and with Ultrasound Alone", Physical Therapy, 1967; 47(7):594–601.

Davick, J. et al. "Distribution and Deposition of Tritiated Cortisol Using Phonophoresis", Physical Therapy, Nov. 1988; 68(11):1672–1675.

Pratzel, H. et al. "Spontaneous and Forced Cutaneous Absorption of Indomethacin in Pigs and Humans", J. Rheumatol., 1986; 13:1122–1125.

Gaertner, W. "Frequency Dependence of Ultrasonic Cavitation", J. of Acoustical Society of America, Nov. 1954; 26(6):977–980.

Benson, H. et al. "Use of Ultrasound to Enhance Percutaneous Absorption of Benzydamine", Physical Therapy; Feb. 1989; 69(2):113–118.

(List continued on next page.)

Primary Examiner—Christopher L. Chin
Assistant Examiner—Ann Y. Lam
(74) Attorney, Agent, or Firm—Moazzam Latimer LLP

(57) ABSTRACT

A non-invasive method of enhancing the permeability of the skin to a biologically active permeant or compound is described utilizing a combination of sonophoresis and chemical enhancers. Synergism brought simultaneously applying iontophoresis, electroporation, mechanical vibrations and magnetophoresis is used to optimize the transcutaneous active permeation of compounds, considerably lowering the time of treatment. The method is intended also for, among others, the non-invasive painless treatment of cellulitis, localized fat, stretch marks and flacid skin.

29 Claims, 5 Drawing Sheets

Perspective view of the experimental equipment and application device

OTHER PUBLICATIONS

Young, J. "Transmission of Sound through Thin Elastic Plates", J. Acoustical Society of America, Jul. 1954; 26(4):485.

Levy, D. et al. "Effect of Ultrasound on Transdermal Drug Delivery to Rats and Guinea Pigs", J. Clin. Invest.; Jun. 1989; vol. 83, No. 6, pp. 2074–2078.

Tyle, P. et al., "Drug Delivery by Phonophoresis", Pharmaceutical Research, 1989; 6:355–61.

Benson, H. et al. "Influence of Ultrasound on the Percutaneous Absorption of Nicotinate Esters", Pharmaceutical Research, Jan. 1991; 8(1):204–209.

Bommannan, D. et al. "Sonophoresis. I. The Use of High–Frequency Ultrasound to Enhance Transdermal Drug Delivery", Pharmaceutical Research, 1992; 9(4):559–564.

* cited by examiner

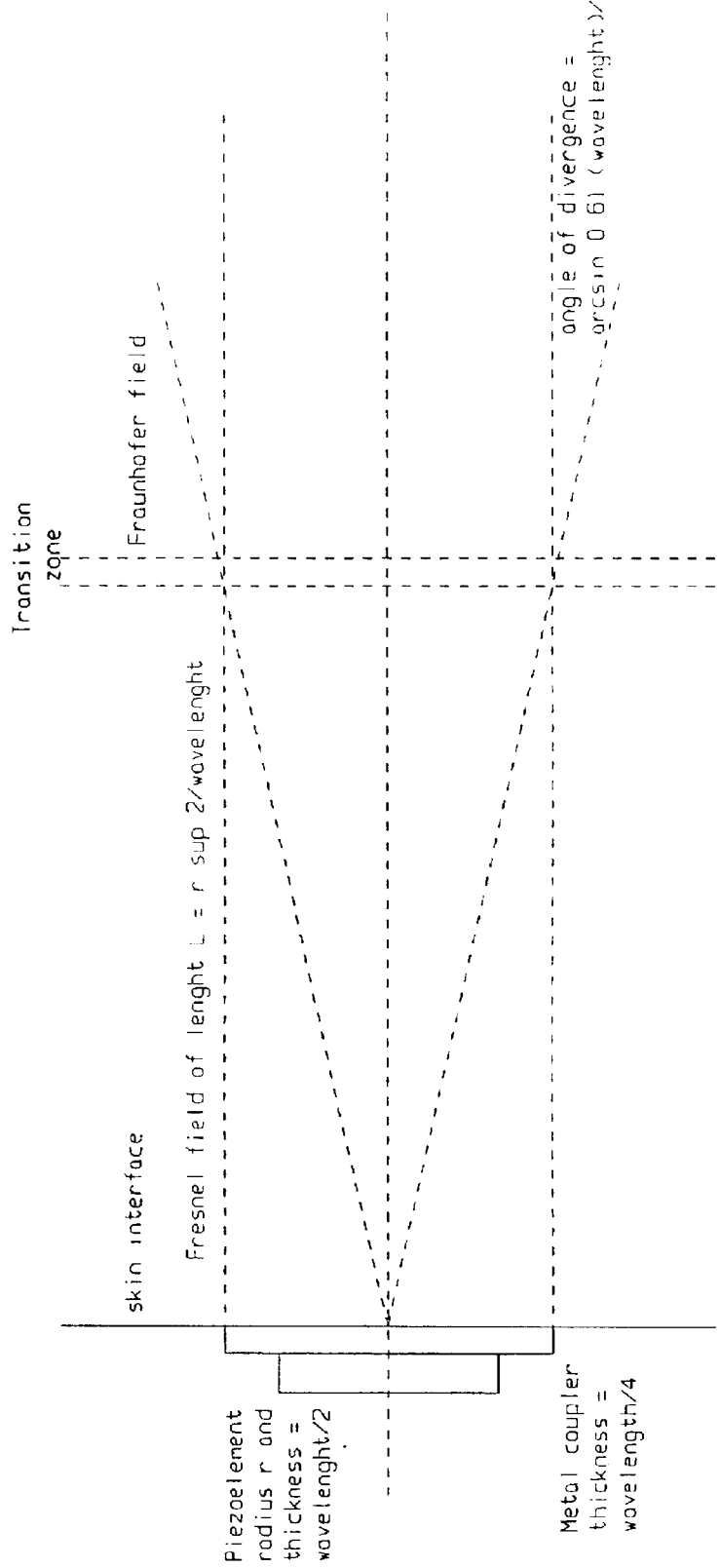
FIG 1 - Fresnel and Fraunhofer ultrasound fields
( not to scale )

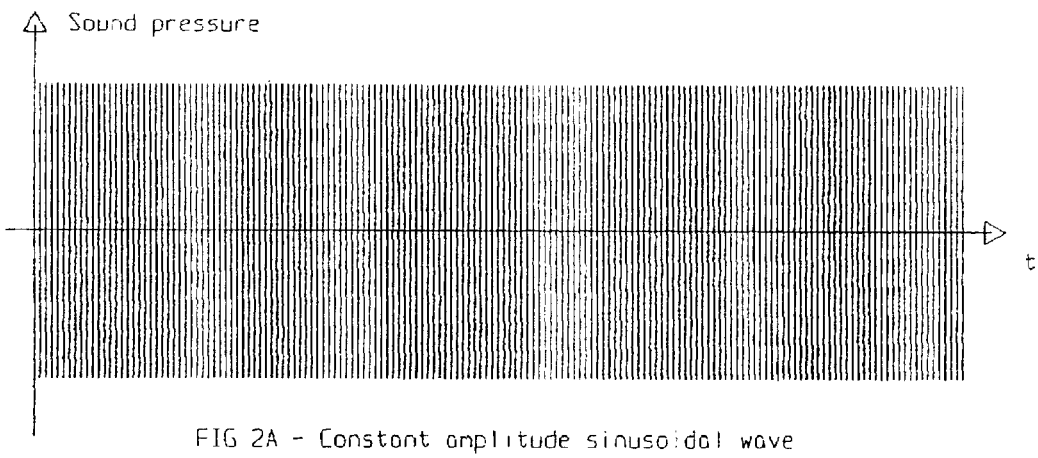
FIG 2A - Constant amplitude sinusoidal wave
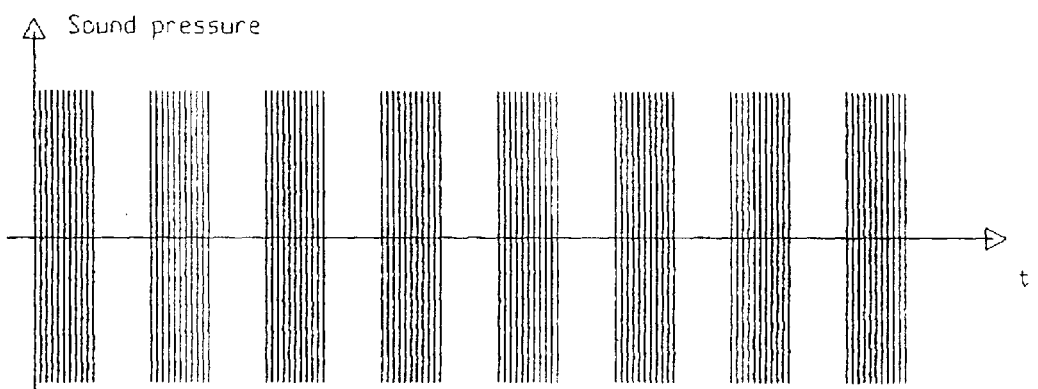
FIG 2B - Sinusoidal wave modulated by a switching signal
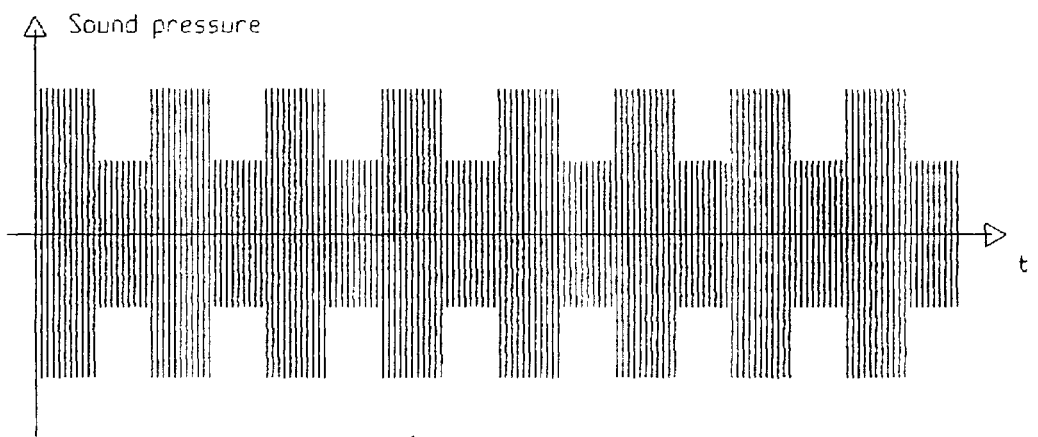
FIG 2C - Amplitude modulated sinusoidal wave

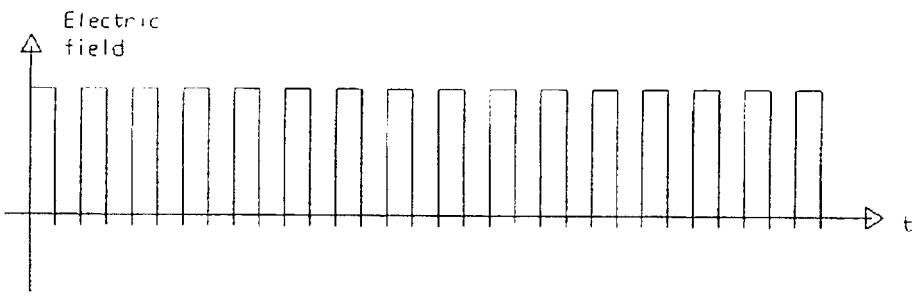
FIG 3A - Rectangular pulses with fixed frequency amplitude and duty cycle
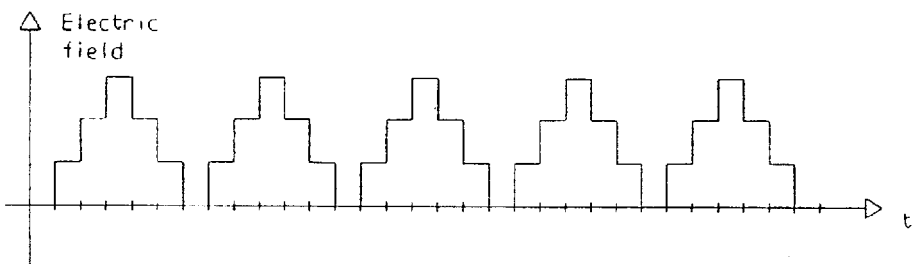
FIG 3B - Constant frequency amplitude modulated wave
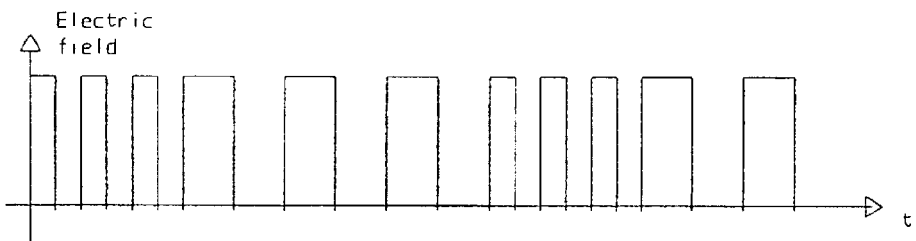
FIG 3C - Frequency modulated constant amplitude rectangular wave
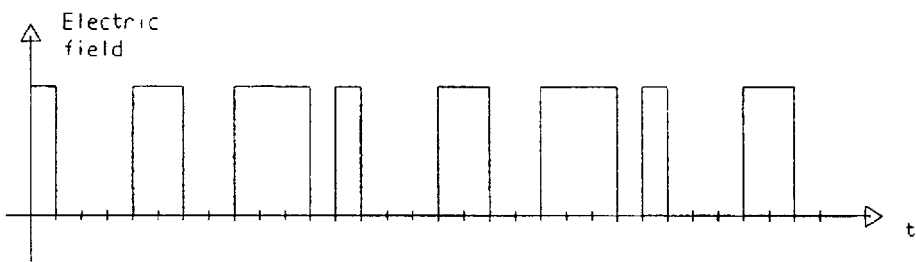
FIG 3D - Constant frequency pulse width modulated rectangular wave
( time varying duty cycle )

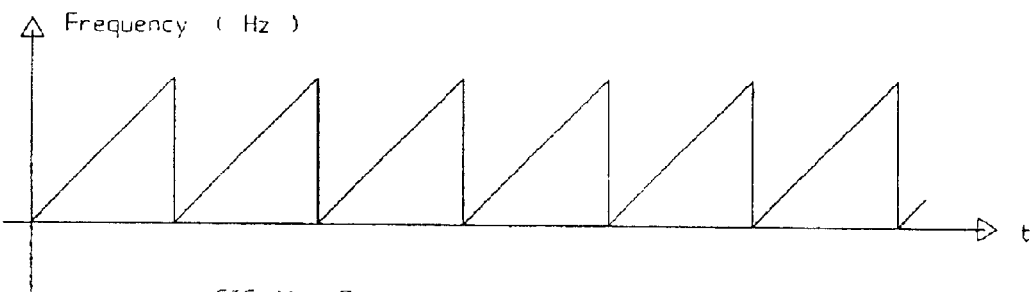
FIG 4A - Frequency varying sawtooth wave
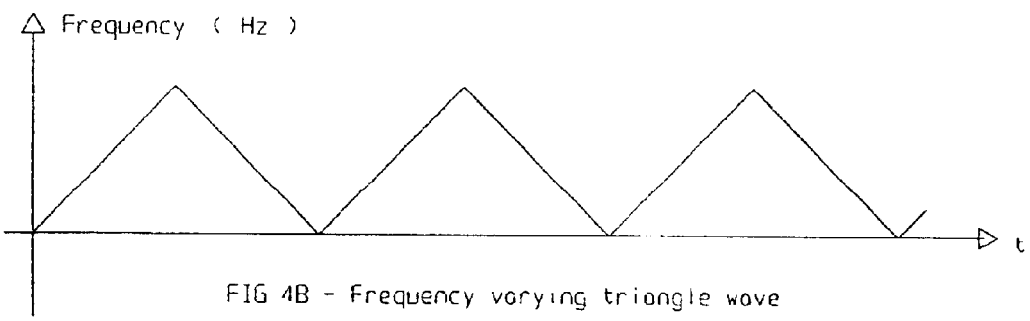
FIG 4B - Frequency varying triangle wave
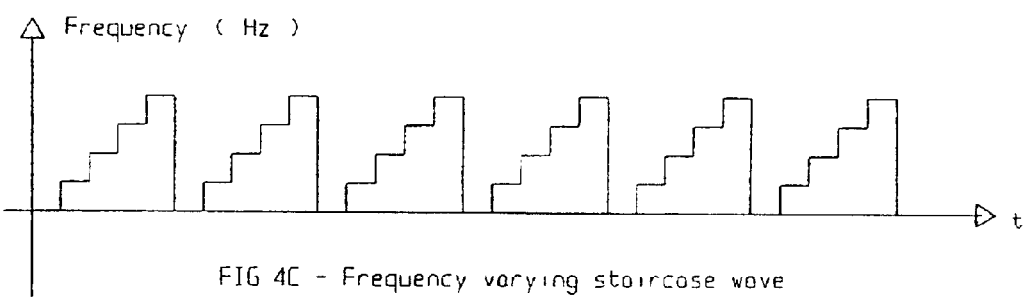
FIG 4C - Frequency varying staircase wave
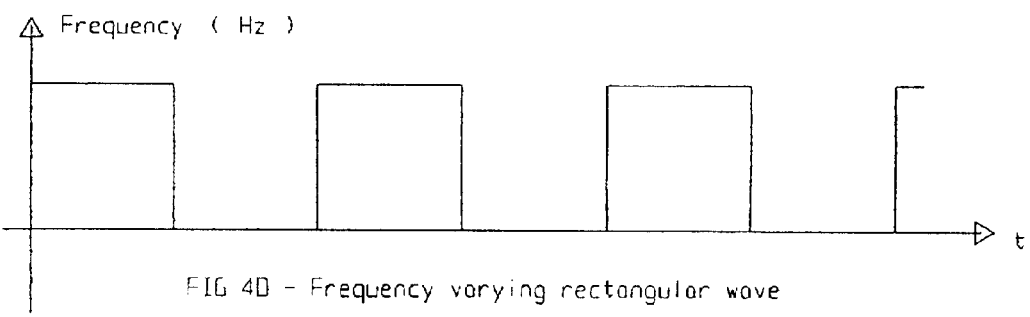
FIG 4D - Frequency varying rectangular wave

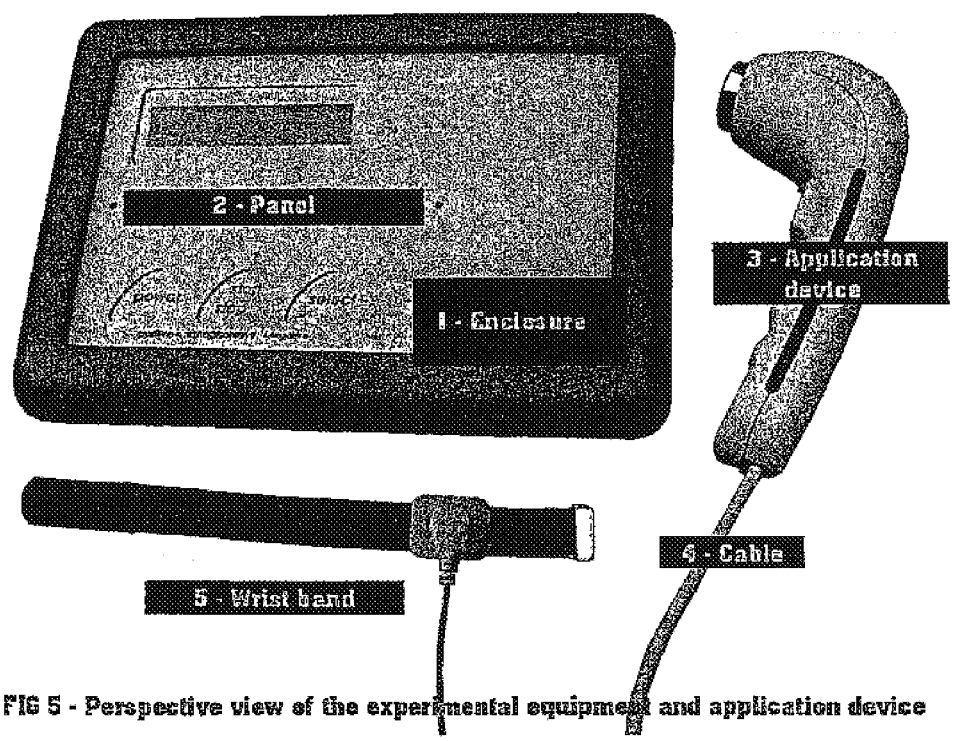
FIG 5 - Perspective view of the experimental equipment and application device

DEVICES AND METHODS FOR PROMOTING TRANSCUTANEOUS MOVEMENT OF SUBSTANCES

BACKGROUND OF THE INVENTION

This invention relates generally to the field of compound delivery for obtaining both local and systemic results. More particularly, it relates to a non-invasive method of compound delivery through the epidermis by means of increasing the permeability of skin through the use of chemical enhancers and sonophoresis and the synergetic simultaneous use of iontophoresis, electroporation, mechanical vibrations and magnetophoresis for optimizing transcutaneous compound delivery into the body.

The human skin has barrier properties and stratum corneum is mostly responsible for them, thus it is exactly the statum corneum, the outer horny layer of the skin, that imposes the greatest barrier to transcutaneous flux of compounds into the body.

The low permeability attributed to the stratum corneum, a complex structure comprised of multi-layered compact keratinized cells; low permeability is due to dead cells filled with keratin fibers (keratinocytes) surrounded by highly-ordered structure of lipid bilayers (Flynn, G. L., In Percutaneous Absorption: Mechanisms-Methodology-Drug Delivery.; Bronaugh, R. L., Maibach, H. I. (Ed), pages 27–53, Marcel Dekker, New York, 1989).

The stratum corneum hasn't constant thickness, since it depends on each particular area, being thinner in areas subject to folds and much thicker in the hands palms and feet soles, is a very resistant waterproof membrane that both protects the body from invasion by exterior substances and the outward migration of fluids and dissolved molecules and creates a mechanical and biological shield between the environment and the interior of the body. The stratum corneum is continuously renewed by shedding of dead cells during desquamation and the formation of new corneum cells by the keratinization process.

Considering the permeation of compounds with non-charged molecules into the skin the flux of said compound across the epidermis is controlled by Fick's First Law which states that this flux depends on the diffusion coefficient and on the gradient of concentration of the compound. One important issue to be remebered is that the diffusion coefficient is strongly dependent on the degree of hydration of the skin, significantly increasing with it.

Therefore one of the ways of enhancing the flux of compounds into the body is through the so-called penetration or chemical enhancers which increase the coefficient of diffusion of the stratum corneum and may be associated with sonophoresis, that is, ultrasound energy.

From the physical standpoint ultrasound waves have been defined as mechanical pressure waves with frequencies above 20 KHz, H. Lutz et al., Manual Of Ultrasound 3–12 (1984), are generated by either natural or synthetic materials that show the so-called piezoelectric property, meaning that these materials both generate an electric field when mechanically stressed (direct piezoelectric effect) and also generate a mechanical force when an electric field is conveniently applied to them (inverse piezoelectric effect).

These properties have been first established by Pierre and Jacques Curie who have observed their ocurrence in natural materials like the Rochelle salt; however in our days synthetic piezoceramic materials are preferred instead due to their more stable properties since they are not hygroscopic and also to the possibility of being manufactured in any shape, allowing a lot of different applications.

Ultrasound has also been used to enhance permeability of the skin and synthetic membranes to compounds and other molecules and its use to increase the permeability of the skin to compound molecules has been called sonophoresis or phonophoresis meaning transportation through sound like waves.

U.S. Pat. No. 4,309,989 to Fahim describes a method of topically applying an effective medication in an emulsion coupling agent by ultrasound. More particularly, a method of treating a skin condition by applying a medication in an emulsion coupling agent and massaging it into the affected area with ultrasonic vibrations thereby causing the medication to penetrate into the skin. Specifically, a method and composition for the treatment of Herpes Simplex Type 1 and Type 2 lesions. Also specifically, a method and composition for the treatment of demidox mites. U.S. Pat. No. 4,372,296 to Fahim similarly describes treatment of acnes by topical application of zinc sulfate and ascorbic acid in a coupling agent.

U.S. Pat. No. 4,767,402 to Kost et al. discloses a method using ultrasound to enhance permeation of molecules through the skin and into the blood stream, at a controlled rate. Depending on the compound being infused through the skin, the rate of permeation is increased as well as the efficiency of transfer. Drugs which may not be effective under other conditions, for example, due to degradation within the gastrointestinal tract, can be effectively conveyed transdermally into the circulatory system by means of ultrasound. Ultrasound is used in the frequency range of between 20 KHz and 10 MHz, the intensity ranging between 0 and 3 W/cm.sup.2. The molecules are either incorporated in a coupling agent or, alternatively, applied through a transdermal patch.

U.S. Pat. No. 4,780,212 to Kost et al. teaches use time, intensity, and frequency control to regulate the permeability of molecules through polymer and biological membranes. Further, the choice of solvents and media containing the molecules also affects permeation of the molecules through the membranes.

U.S. Pat. No. 4,821,740 to Tachibana et al. discloses an endermic application kit for external medicines, which comprises a drug-containing layer as provided near an ultrasonic oscillator. The kit includes a cylindrical fixed-type or portable-type and a flat regular-type or adhesive-type, and the adhesive-type may be flexible and elastic. The drug absorption is ensured by the action of the ultrasonic waves from the oscillator and the drug release can be controlled by varying the ultrasonic wave output from the oscillator.

U.S. Pat. No. 5,007,438 to Tachibana et al. is described an application kit in which a layer of medication and an ultrasound transducer are disposed within an enclosure. The transducer may be battery powered. Ultrasound causes the medication to move from the device to the skin and then the ultrasound energy can be varied to control the rate of administration through the skin.

U.S. Pat. No. 5,115,805 to Bommannan et al. discloses a method for enhancing the permeability of the skin or other biological membrane to a material such as a drug is disclosed. In the method, the drug is delivered in conjunction with ultrasound having a frequency of above about 10 MHz. The method may also be used in conjunction with chemical permeation enhancers and/or with iontophoresis. It is informed but not shown that chemical penetration enhancers and/or iontophoresis could be used in connection with the ultrasound treatment.

U.S. Pat. No. 5,444,611 to Eppstein et al. describes a method of enhancing the permeability of the skin or mucosa to a biologically active permeant or drug utilizing ultrasound or ultrasound plus a chemical enhancer.

Ultrasound can be modulated and frequency modulated ultrasound from high to low frequency can develop a local pressure gradient directed into the body. The method is also useful as a means for application of a tatoo by nininvasively delivering a pigment through the skin surface. Due to the completeness of that disclosure, the information and terminology utilized therein are incorporated herein by reference.

U.S. Pat. No. 6,041,253 to Kost et al. describes a method for transdermal transport of molecules during sonophoresis (delivery or extraction) further enhanced by application of an electric field, for example electroporation of iontophoresis. This method provides higher drug transdermal fluxes, allows rapid control of transdermal fluxes, and allows drug delivery or analyte extraction at lower ultrasound intensities than when ultrasound is applied in the absence of an electric field. Due to the completeness of that disclosure, the information and terminology utilized therein are incorporated herein by reference.

U.S. Pat. No. 6,234,990 to Rowe et al. discloses methods and devices for application of ultrasound to a small area of skin for enhancing trasdermal transport. An ultrasound beam having a first focal diameter is channelled into a beam having a second,smaller diameter without substantial loss of energy. A two step noninvasive method involves application of ultrasound to increase skin permeability and removal of ultrasound followed by transdermal transport that can be further enhanced using a physical enhancer. Due to the completeness of that disclosure, the information and terminology utilized therein are incorporated herein by reference.

Many other references teach use of ultrasound to deliver drugs through the skin, including Do Levy et al., 83 J. Clin. Invest. 2074 (1989); P. Tyle & P. Agrawala, 6 Pharmaceutical Res. 355 (1989); F. L. Henley, $65^{th}$ Annual Conference of the American Physical Therapy Association, Anhaheim, Calif. (1990); H. Benson et al., 8 Pharmaceutical Res. (1991); D. Bommannan et al., 9 Pharmaceutical Res. 559 (1992); K. Tachibana, 9 Pharmaceutical Res. 952 (1992); T. Wong, Proceedings of the Joint Congress of the American Physical Therapy Association, Toronto, Ontario, Canada (1994); N. N. Byl, Physical Therapy, Volume 75, Number 6, (1995).

Many authors report the success of application of sonophoresis, J. Griffin & J. Touchstone, 42 Am. J. Phys. Med. 77 (1963); J. Griffin et al., 44 Am. J. Phys. Med. 20 (1965); J. Griffin et al., 47 Phys. Ther. 594 (1967); J. Davick et al., 68 Phys. Ther. 1672 (1988); D. Bommannan et al., 9 Pharm. Res. 559 (1992), while others have obtained negative results, J. McElnay et al., 20 Br. J. Clin. Pharmacol. 4221 (1985); H. Pratzel et al., 13 J. Rheumatol. 1122 (1986); H. Benson et al., 69 Phys. Ther. 113 (1988).

However recent studies of sonophoresis show that application of ultrasound at therapeutic frequencies of about 1 MHz induces growth and oscillations of air pockets present in the keratinocytes of the stratum corneum disorganizing the stratum corneum lipid bilayers thereby enhancing transcutaneous transport.

This means that permeation using only chemical enhancers and sonophoresis seems to be a limited process, therefore other physical principles must be added to improve the process in order to create a method for actively and safely enhancing the flux rate of compounds into the skin to a greater extent than can be achieved without their use.

From now on we will be concerned with ionic permeation, the transportation of charged particles, then we have to consider the general diffusion equation instead where Fick's First Law must be added of a second term, an electric potencial gradient term, meaning another driving force created by an electrical field applied between the area under treatment and a referencial electrode, the so-called process of iontophoresis.

Electroporation is believed to work in part by creating transient pores in the lipid bilayers of the stratum corneum (Burnett (1989)).

Iontophoresis involves the topical delivery of either an ionized form of compound or an unionized compound carried with the water flux associated with ion transport, the process being termed electro-osmosis.

An electrical field is created between the area under treatment and a referencial electrode usually fixed to the right wrist of the individual, normally consisting of a variable electric field with selected properties like amplitude frequency, waveshape, polarity and duty cycle.

The polarity of the electric field depends on the pH of the chemicals to be delivered into the skin, therefore it must be accordingly selected by the user.

Low and medium frequency periodic mechanical vibrations created for example by rotating unbalanced masses applied to the skin surface create mechanical pressure waves that establish a pumping action, forcing the compounds into the skin, enhancing the permeation process.

Optimum results are obtained using time varying vibrations, resulting in several types of complex waveshapes like "sawtooth", "triangle", "on-off" and "staircase" among others, with fundamental frequencies in the range of 1 Hz to 1 KHz, but with several useful low order harmonic terms having amplitudes, frequencies and phases according to their respective expansion using Fourier's series.

Finally, one more physical principles can be used to achieve further enhancement of flux rate: constant or time varying magnetic fields which can induce mechanical forces to charged particles in such a way to force them into the skin, the so-called process of magnetophoresis.

It is worthwhile to remember that also some heat is internally generated by sonophoresis and additionally also iontophoresis contributes with Joule's effect originated heat, all them giving some contribution to the increase of temperature of the skin, thus some prevision must be made to keep this temperature under control.

OBJECTS AND SUMMARY OF THE INVENTION

An object of the present invention is to provide a method for fast active transcutaneous permeation of compounds through the human skin targeting obtaining either local or systemic results allowing,among others, the non-invasive painless treatment of cellulitis, localized fat, stretch marks and flacid skin.

Another object of the invention is to provide a method for the active transcutaneous permeation of compounds in a non invasive basis, allowing treatments with minimal occurrence of undesirable collateral effects.

A further object of the invention is to minimize the time of treatment through the synergetic simultaneous use of both chemical enhancers and several physical principles.

These and other objects may be accomplished by applying to the skin surface permeation enhancers and compounds simultaneously with physical permeability enhancers such as sonophoresis with modulated or non-modulated ultrasound, continuous or pulsed, iontophoresis, electroporation, mechanical vibrations and magnetophoresis.

Specially designed equipment and application device allowing the application of this method will be described herein.

Ultrasound energy also may also open up diffusional pathways in the stratum corneum, causing an increase in the permeability of that layer and causing frictional heat to be generated in deeper tissues, increasing the activity of both lymph and blood circulation, as well as of metabolic processes.

Due to the complete synergism and complementarity of these physical principles, their combined actions lead us to fast treatments when associated with ultrasound coupling products, chemical permeants, allowing compounds to be efficiently permeated through the skin, since both ultrasound, iontophoresis, electroporation, mechanical vibrations and magnetophoresis force chemical enhancers and compounds into the stratum corneum, thereby reducing the lag time associated with the non-enhanced (passive) diffusion process.

BRIEF DESCRIPTION OF THE DRAWINGS

FIG. 1 shows the distribution of energy fields produced by an ultrasound transducer and division into near field (Fresnel field) and far field (Fraunhofer field).

FIG. 2A shows an example of continuous non-modulated ultrasound wave.

FIG. 2B shows an example of pulsed ultrasound wave.

FIG. 2C shows an example of amplitude modulated ultrasound wave.

FIG. 3A shows an example of non modulated electrical field according to the present invention.

FIG. 3B shows an example of amplitude modulated electrical field according to the present invention.

FIG. 3C shows an example of frequency modulated electrical field according to the present invention.

FIG. 3D shows an example of duty cycle modulated electric field according to the present invention.

FIG. 4A shows an example of "sawtooth" frequency waveshape for mechanical vibrations according to the present invention.

FIG. 4B shows an example of "triangle" frequency waveshape for mechanical vibrations according to the present invention.

FIG. 4C shows an example of "staircase" frequency waveshape for mechanical vibrations according to the present invention.

FIG. 4D shows an example of "on-off" frequency waveshape for mechanical vibrations according to the present invention.

FIG. 5—Perspective view of an experimental equipment and application device suitable for the purposes of this invention.

DETAILED DESCRIPTION OF THE INVENTION

Although the present invention, as described herein, presents the best approach presently known for enhancing the permeability of membranes using ultrasound and enhancing the transcutaneous flux rate of a compound through a biological membrane through the use of chemical permants and iontophoresis, electroporation, mechanical vibrations and magnetophoreis, it is to be understood that this invention is not limited to the particular process steps and materials disclosed herein as such process steps and materials may vary.

It is also to be understood that the terminology used herein is not intended to be limiting since the scope of the present invention will be limited only by the appended claims and their equivalents.

This invention is intended to establish an optimized mode of delivery of agents or permeants which exist in the state of the art or which may later be established as active agents and which are suitable for delivery by the present invention, including compounds normally delivered into the body, through body surfaces and membranes, including skin.

As used herein, a "biological membrane" is intended to mean also the human skin.

As used herein, "individual" refers to a human, to which the present invention may be applied.

As used herein, "transcutaneous flux rate" is the rate of passage of any compound, pharmacologically active agent, through the skin of an individual.

As used herein, "non-invasive" means not requiring the entry of a needle, catheter, or other invasive medical instrument into any part of the body including its natural orifices like mouth, nose, ears, anus, urethra and vagina.

Firstly speaking of permeation of non charged particles, Fick's First Law states that the flux of a compound across the skin can be altered by changing either the the diffusion coefficient or the driving force, that is the gradient of concentration. In a simplified way this means that if the gradient of concentration is constant, then the transcutaneous flux rate can only be enhanced by improving the diffusion coefficient. This can be achieved by the use of so-called penetration or chemical enhancers associated with sonophoresis.

There are two primary categories of components where chemical enhancers are comprised of, that is, cell-envelope disordering compounds and solvents or binary systems containing both cell-envelope disordering compounds and solvents, where the first are well known as being useful in topical pharmaceutical preparations therefore any cell envelope disordering compound is useful for purposes of this invention.

Cell-envelope disordering compounds are thought to assist in skin penetration by disordering the lipid structure of the stratum corneum cell-envelopes; solvents include water; diols, mono-alcohols, DMSO and others.

European Patent Application 43,738 presents the use of selected diols as solvents along with a broad category of cell-envelope disordering compounds for delivery of lipophilic pharmacologically-active compounds. Because of the detail in disclosing the cell-envelope disordering compounds and the diols, this disclosure of European Patent Application 43,738 is incorporated herein by reference.

Other chemical enhancers, not necessarily associated with binary systems, include DMSO or aqueous solutions of DMSO such as taught in Herschler, U.S. Pat. No. 3,551,554; Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

Some chemical enhancer systems may show negative colateral effects such as toxicity and skin irritation. U.S. Pat.

No. 4,855,298 discloses compositions for reducing skin irritation having an amount of glycerin sufficient to provide an anti-irritating effect.

Since this invention is not drawn to the use of chemical enhancers per se it is believed that all chemical enhancers useful in the delivery of compounds through the skin may be associated with sonophoresis, iontophoresis, mechanical vibrations and magnetophoresis in further enhancing the delivery of permeants and compounds through the skin surface.

Permeation through the stratum corneum can occur either by intracellular, intercellular or transappendageal penetration, in this case specially through the aqueous pathway of the sweat glands. The property shown by the ultrasound of enhancing the permeability of the stratum corneum and, consequently, increasing transcutaneous flux rate is thought to derive from thermal and mechanical alteration of biological tissues.

The physical properties of ultrasound waves that can be changed either to control or improve penetration include frequency and intensity along with time of application. Other factors are also important, for example the composition and structure of the membrane through which molecules are to be transported, the physical and chemical characteristics of the medium in which the molecules are suspended, and the nature of the molecules themselves.

The exposure may be either continuous or pulsed to reduce excessive heating of biological membranes, when upper average values of usual intensities in the range of 0.01–2.5 W/cm.sup.2 are used; Selection is made in such a way to intensity be high enough to achieve the desired results as well as low enough to avoid significant increase of skin temperature. However, using our experimental equipment and application device intensities between 0.3 and 1.5 W/cm.sup.2 have shown to give good results when the process is associated with simultaneous application of iontophoresis.

Used frequencies varied from 20 kHz to 10 MHz, preferably 1 to 5 MHz taking into account that the practical depth of penetration of ultrasonic energy into living soft tissue due to attenuation is inversely proportional to the frequency; high frequencies have been suggested to improve drug penetration through the skin by concentrating their effect in the stratum corneum but frequencies between 1 to 3 MHz show a better overall efficiency since they create some deeper internal heat producing a temperature rise that speeds up metabolic processes in the area under treatment.

No significant cavitational effects have been observed in fluids at ultrasound frequencies greater than 2.5 MHz, due to the fact that these cavitational effects vary inversely with ultrasound frequency [Gaertner, W., Frequency dependence of ultrasonic cavitation, J. Acoust. Soc. Am., 26:977–80 (1984)], therefore 2.5 MHz is considered a reasonable estimate of the upper frequency limit for the occurrence of cavitation in fluids at therapeutic ultrasound intensities. Hence, since cavitation plays an important role in transcutaneous permeation, the synergistic effect of sonophoresis and iontophoresis shall be nearly absent with frequencies higher than 2.5 MHz.

As far as the use of ultrasound for compound delivery is known, results have been largely disappointing in that enhancement of permeability has been relatively lower than expected causing no consensus on the efficacy of ultrasound for increasing compound flux across the skin, suggesting that other driving forces must also be used.

When ultrasound energy is applied into the body using for example a circular plane metallic transducer two fields are created, the near field, known as Fresnel field and the far field, known as Fraunhofer field as shown in FIG. 1.

In Fresnel field ultrasound energy radiated from different parts of the element travels as spherical waves that interfere both constructively and destructively; thus there are zones of maxima and minima of mechanical pressure along and across the beam. This field is characterized by a length L which depends on the radius of the radiant surface and the wavelenght of the ultrasound in the medium in front of it, i.e., the skin and soft tissues beneath it.

Therefore the ultrasound energy distribution pattern shows a large number of closely spaced local mechanical pressure peaks and nulls. The energy is "channeled" into the skin in an structure having parallel "walls" orthogonal to the plane of the transducer face.

In Fraunhofer field the ultrasound beam diverges in such a way which also depends on the radius of the radiant surface and the wavelenght of the ultrasound in the medium, usually soft tissues, meaning that in Fraunhofer field the energy is spreaded in a conic distribution.

The interface of the piezoelectric transducer with the individual is reflective due to the different values of their respective acoustic characteristic impedances and energy is reflected back to the piezoelement. Thus, in order to obtain constructive interference, that is reinforcement of the ultrasound waves, the thickness of the piezoelectric transducer, normally circular shaped, must be one-half wavelenght for the frequency used.

In our experiments our application device used a lead zirconate titanate transducer 2 mm thick, and since the speed of sound for this material is of 4000 m/sec, the frequency which allows maximum energy transfer for such device is of 1 MHz.

By many reasons the individual must be mechanically isolated from the piezoelectric element, and usually this is achieved interposing a plate of material having an intermediate acoustic characteristic impedance between them; in order to maximize the energy transfer, this plate must have a thickness of one quarter wavelenght for the frequency being used.

Our application device used an aluminium plate for this purpose and since the speed of sound for this material is of 6400 m/s then best results were obtained with a plate 1.6 mm thick.

In order to minimize reflexions of the ultrasonic beam, which depend on the ratio of the acoustic characteristic impedances of the media it is crossing we must avoid any air gap in the interface between the application device and the surface of the skin. Thus a coupling agent, preferably one having a low absorption coefficient of ultrasound energy and being non-staining, non-irritating and slow drying must be topically applied to the skin to efficiently transfer the ultrasonic energy from the ultrasound transducer into the skin.

This way the ultrasound coupling agent can be also formulated along with chemical enhancers and drugs to be permeated, the resulting compounds known as "melanges".

The above description shows that each particular application device must be operated in a single frequency, otherwise internal acoustic mismatches will cause only partial transfer of energy to the individual, decreasing the efficiency of the process.

Besides this, there will be a considerable overheating of the transducer created by the internal reflected waves, which can negatively affect the mechanical integrity of the transducer, as well as causing a degradation of its piezoelectric properties along the time.

Some different patterns of peaks and nulls can be obtained with non-modulated ultrasound energy mechanically travelling the transducer back and forth on the surface of the area under treatment, since the results will be quite similar to an "on-off" amplitude modulation, displacing the areas of maxima and minima of pressure along the time.

Application of electric current enhances transcutaneous transport by different mechanisms, for example it provides an additional driving force for the transport of charged molecules across the skin since electrical current paths can be established through the intercellular spaces of the cells of the stratum corneum and second, ionic motion due to application of electric fields may induce convective flows across the skin, referred to as electroosmosis, an important mechanism in transcutaneous transport of neutral molecules during iontophoresis.

Also and it is thought to have additional paths through the salty sweat glands fluids which show a low electrical impedance to the current flow due to the conductive nature of sweat.

Frequencies can range from 5 KHz to 1 MHz, often in the range of 50 KHz to 100 KHz and rectangular voltage with amplitudes from 0 to 15 V or current waves with amplitudes from 0 to 1.0 $mA/cm.sup.2$ with properly selected duty cycles are convenient to achieve good results.

At these frequencies the capacitive reactances of the cells are negligible compared to their ohmic resistances, therefore the intensity of the current is mostly governed by the ohmic resistance (L. A. Geddes, L. E. Baker, Applied Biomedical Instrumentation, John Wiley & Sons, New York, 1989).

Therefore current waves obtained through electronic generators having high internal impedance are preferred instead since their amplitudes don't depend on fluctuactions on the value of skin electrical impedance, allowing safer and more reliable treatments.

Amplitudes shall be kept small enough not to originate either tissue electrical stimulation or excessive heat due to Joule effect. Good results have been obtained with values about 0.5 $mA/cm.sup.2$.

Mechanical vibrations create pressure gradients which enhance the physical movement of compounds into the skin, improve both lymph and blood circulation in the area as well as create physical stimuli which have a physiological response from the individual, since pressure sensitive nervous terminations of tissues in the area being treated are stimulated and respond to these stimuli increasing the speed of some metabolic processes.

These pressure waves are inertially created through an unbalanced rotating mass fixed to the shaft of a direct current (DC) micromotor having its speed controlled by a pulse width modulation technique (PWM), allowing time varying speeds to be synthesized.

In our experiences several different frequency waveshapes have been used, i.e., sawtooth, triangle, on-off, staircase, constant low speed, constant high speed, periodic switching from low to high speed as well as any combinations of them; all time varying frequency waveshapes have given better results, probably due to time varying pressure gradients created as well as the property of the individual to have better perception and responses to changes; of course other waveshapes can be used with the present invention.

Magnetophoresis in based on the law of Electromagnetism which states that when charged particles cross a magnetic field they are subject to the action of forces; thus charged molecules of chemicals being permeated can further have a driving force applied to them by means of convenient magnetic fields having such magnitude, direction and polarity in order to enhance the process of transcutaneous permeation.

These magnetic fields may be created by the circulation of electric currents through specially developed coils placed inside the application device.

EXPERIMENTAL EQUIPMENT AND APPLICATION DEVICE

In order to have a better understanding of both the equipment and the application device created for the purposes of this invention, it will be described making reference to FIG. 5 where a perspective view is shown.

According to this drawing, the experimental equipment consists of a main unit comprised of an enclosure (#1), which can be metallic, plastic or using any other similar materials, which encloses all electronic circuitry needed for its operation.

At the front part of this main unit (#1) there is a panel (#2) with several controls, displays and signaling devices in order to allow an interfacing with the user as friendly as possible.

The equipment also has a manual application device (#3) made of plastic, metal and/or similar materials connected to the main unit (#1) by an electrical cable (#4) using an appropriate connector.

A conductive wrist band (#5) is used to connect the main unit to the individual under treatment through an helicoidal electrical cable.

The application device has an internal ultrasound transducer for the generation of 1 MHz ultrasound waves for sonophoresis, mechanically coupled to a 35 mm metallic circular plate, designed to achieve best enhancement in the skin permeability as described herein.

Either iontophoresis and electroporation may be obtained through the application of an electric variable field between the metallic surface of the apllication device and the skin, the electric path being closed through the conductive wrist band attached to the wrist of the individual under treatment.

A switch was included in order to reverse the polarity of the electric field according to the pH of the melange being used; this switching action can be achieved electronically. Amplitude, frequency and duty cycle of a rectangular current wave have were modulated targeting best results; also pulsed rectangular waves have been used for the same purpose.

Amplitudes of currents have been varied in the range of 0.1 to about 1 $mA/cm.sup.2$ with better results obtained for currents higher than 0.5 $mA/cm.sup.2$.

Low frequency mechanical vibrations are generated internally to the application device by means of an internal unbalanced rotating mass with speed controlled through pulse width modulating the DC voltage applied to the driving electric DC micromotor. Frequencies of 1 Hz to 200 Hz were used with several speed waveshapes as previously described.

Both constant and variable magnitude magnetic field are generated by electrical currents passing through a special coil internal to the application device.

Since also some spatially distributed internal heat is generated by sonophoresis and also conductive heating is produced by Joule effect at the face of the metallic plate of the application device, temperature of the application device is continuously sensed through a thermal sensor allowing this temperature to be always kept under 41.degree.C., using a microcontroller and associate electronic circuitry.

This way in normal use some drops of the melange to be permeated into the skin are topically dispensed and them the application device is moved in circular patterns over the skin covering the area under treatment till the complete permeation of the melange is achieved.

Results obtained in treatments of cellulitis, localized fat, stretch marks and flacid skin with special melanges were encouraging, showing the validity of both the processes and the method of application used.

The above examples and illustrated embodiments are but representative of systems which may be employed in the utilization of one or more chemical and/or physical enhancement means for the transcutaneous delivery of permeants and compounds.

The invention is directed to the discovery that the proper use of chemical enhancers and ultrasound associated with the simultaneous use of further physical principles through a single application device as described herein enables the noninvasive transcutaneous delivery of compounds.

However, the invention is not limited only to the specific illustrations since there are numerous enhancer systems some of which may function better than another for delivery of permeants and compounds.

Therefore, the invention is limited in scope only by the mentioned claims and functional equivalents thereof.

What is claimed is:

1. A method for enhancing the transcutaneous flux rate of an active permeant into a body using a single compact, portable device the method comprising:

applying the active permeant to a surface of the body along with simultaneous, separate and distinct sources of sonophoresis, mechanical vibrations at a frequency less than ultrasound and magnetophoresis, and at least one of iontophoresis or electroporation, for a time period and with physical properties effective to enhance the transcutaneous flux rate into the body.

2. The method of claim 1, further comprising:

applying a chemical permeation enhancer to the surface of the body along with the application of the active permeant.

3. The method of claim 1, wherein the sources comprise a plurality of transducers, each transducer producing a separate and distinct output.

4. The method of claim 3, wherein the plurality of transducers are housed within a single applicator.

5. The method of claim 3, wherein the sonophoresis includes a frequency in the range of about 20 KHz to 10 MHz.

6. The method of claim 1, wherein the sonophoresis includes a modulated, pulsed wave.

7. The method of claim 1, wherein the iontophoresis or electroporation comprises an electric field ranging from 0.1 to 25 V.

8. The method of claim 1, wherein the mechanical vibrations have frequencies ranging from 1 Hz to 1 KHz.

9. The method of claim 1, further comprising:

maintaining any heat generated at the surface of the body to stay below 41 degrees Celsius.

10. The method of claim 1, wherein the time period is in the range of about 1 to 40 minutes.

11. A compact, portable device for enhancing the transcutaneous flux rate of an active permeant into a body, the device comprising:

separate and distinct sources of sonophoresis, mechanical vibrations at a frequency less than ultrasound and magnetophoresis, and at least one of iontophoresis or electroporation;

wherein the sources, when simultaneously applied for an effective time period and with effective physical properties to a surface of the body in contact with the active permeant, enhance the transcutaneous flux rate of the active permeant into the body.

12. The device of claim 11, wherein the sources further enhance transcutaneous flux when a chemical permeation enhancer is applied to the surface of the body along with the application of the active permeant.

13. The device of claim 11, wherein the sources comprise a plurality of transducers, each transducer producing a separate and distinct output.

14. The device of claim 13, wherein the plurality of transducers are housed within a single applicator.

15. The device of claim 11, wherein the sonophoresis includes a frequency in the range of about 20 KHz to 10 MHz.

16. The device of claim 11, wherein the sonophoresis includes a modulated, pulsed wave.

17. The device of claim 11, wherein the iontophoresis or electroporation comprises an electric field ranging from 0.1 to 25 V.

18. The device of claim 11, wherein the mechanical vibrations have frequencies ranging from 1 Hz to 1 KHz.

19. The device of claim 11, further comprising:

means for maintaining the temperature of the surface of the body to stay below 41 degrees Celsius.

20. The device of claim 11, wherein the time period is in the range of about 1 to 40 minutes.

21. A compact, portable device for enhancing the transcutaneous flux rate of an active permeant into a body, the device comprising:

separate and distinct means for production of sonophoresis, mechanical vibrations at a frequency less than ultrasound and magnetophoresis, and at least one of iontophoresis or electroporation;

wherein the means for production, when simultaneously applied for an effective time period and with effective physical properties to a surface of the body in contact with the active permeant, enhance the transcutaneous flux rate of the active permeant into the body.

22. The device of claim 21, wherein the means for production further enhance transcutaneous flux when a chemical permeation enhancer is applied to the surface of the body along with the application of the active permeant.

23. The device of claim 21, wherein the means for production include a plurality of transducers, each transducer producing a separate and distinct output.

24. The device of claim 23, wherein the plurality of transducers are housed within a single applicator.

25. The device of claim 21, wherein the sonophoresis includes a frequency in the range of about 20 KHz to 10 MHz.

26. The device of claim 21, wherein the iontophoresis or electroporation comprises an electric field ranging from 0.1 to 25 V.

27. The device of claim 21, wherein the mechanical vibrations have frequencies ranging from 1 Hz to 1 KHz.

28. The device of claim 21, further comprising:

means for maintaining the temperature of the surface of the body to stay below 41 degrees Celsius.

29. The device of claim 21, wherein the time period is in the range of about 1 to 40 minutes.

* * * * *